(12) United States Patent
Gutbrod et al.

(10) Patent No.: US 10,918,299 B2
(45) Date of Patent: *Feb. 16, 2021

(54) DYNAMIC REPOLARIZATION SUBSTRATE MAPPING

(71) Applicant: Boston Scientific Scimed Inc., Maple Grove, MN (US)

(72) Inventors: Sarah R. Gutbrod, St. Paul, MN (US); Jacob I. Laughner, St. Paul, MN (US); Allan C. Shuros, St. Paul, MN (US); Matthew S. Sulkin, New Brighton, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 214 days.

This patent is subject to a terminal disclaimer.

(21) Appl. No.: 16/013,809

(22) Filed: Jun. 20, 2018

(65) Prior Publication Data
US 2018/0368714 A1 Dec. 27, 2018

Related U.S. Application Data

(60) Provisional application No. 62/523,179, filed on Jun. 21, 2017.

(51) Int. Cl.
*A61B 5/04* (2006.01)
*A61B 5/044* (2006.01)
(Continued)

(52) U.S. Cl.
CPC .......... *A61B 5/044* (2013.01); *A61B 5/04012* (2013.01); *A61B 5/0422* (2013.01);
(Continued)

(58) Field of Classification Search
CPC .... G16H 40/63; A61B 5/044; A61B 5/04012; A61B 5/6858; A61B 5/743; A61B 5/0422;
(Continued)

(56) References Cited

U.S. PATENT DOCUMENTS 6,070,094 A 5/2000 Swanson et al.
6,233,491 B1 5/2001 Kordis et al.
(Continued)

OTHER PUBLICATIONS

Danielle Denisko et al., "Analysis of Activation-Recovery Intervals from Intra-cardiac Electrograms in a Pre-clinical Chronic Model of Myocardial Infarcation", Department of Medical Biophysics, University of Toronto, Toronto, Canada, Springer International Publishing AG (2017); M. Pop and G.A. Wrights (Eds.): FIMH 2017, LNCS 10263, pp. 280-288, 2017.
(Continued)

*Primary Examiner* — Rex R Holmes
(74) *Attorney, Agent, or Firm* — Faegre Drinker Biddle & Reath LLP

(57) ABSTRACT

Methods and systems for cardiac mapping are disclosed. An example system includes a catheter shaft with one or more electrodes coupled to a distal end of the catheter shaft. Electrodes sense electrical signals at anatomical locations within a heart. A processor coupled to the catheter shaft acquires electrogram signals of the heart using the electrodes. Each electrogram signal relates to three-dimensional positional data corresponding to the anatomical locations. The processor also store the electrogram signals of the heart corresponding to electrical activities sensed at corresponding anatomical locations, calculate an activation recovery interval associated with each of the corresponding anatomical locations, determine spatial gradient data of the activation recovery interval based on a distance between at least two neighboring anatomical locations. The system also includes a display device to display a three-dimensional graphical representation of the spatial gradient data between the at least two neighboring anatomical.

9 Claims, 8 Drawing Sheets

(51) Int. Cl.
*A61B 5/042* (2006.01)
*A61B 5/00* (2006.01)
*G16H 40/63* (2018.01)
*A61B 34/20* (2016.01)
*A61B 18/14* (2006.01)
*A61B 18/00* (2006.01)

(52) U.S. Cl.
CPC ............ *A61B 5/6858* (2013.01); *A61B 5/743* (2013.01); *G16H 40/63* (2018.01); *A61B 5/7253* (2013.01); *A61B 18/1492* (2013.01); *A61B 34/20* (2016.02); *A61B 2018/00351* (2013.01); *A61B 2018/00577* (2013.01); *A61B 2034/2051* (2016.02)

(58) Field of Classification Search
CPC .................. A61B 5/7253; A61B 34/20; A61B 2018/00351; A61B 2018/00577; A61B 18/1492; A61B 2034/2051
See application file for complete search history.

(56) References Cited

U.S. PATENT DOCUMENTS

| 6,735,465 | B2 | 5/2004 | Panescu |
| 2011/0137362 | A1 | 6/2011 | Foreman et al. |
| 2012/0101398 | A1* | 4/2012 | Ramanathan ......... A61B 5/044 600/523 |
| 2014/0005563 | A1 | 1/2014 | Ramanathan et al. |

OTHER PUBLICATIONS

International Search Report and Written Opinion issued in PCT/US2018/038641, dated Sep. 7, 2018, 14 pages.

Ramanathan et al., "Activation and repolarization of the normal human heart under complete physiological conditions", Proceedings of the National Academy of Sciences, vol. 103, No. 16, Apr. 18, 2006, pp. 6309-6314.

* cited by examiner

DYNAMIC REPOLARIZATION SUBSTRATE MAPPING

CROSS-REFERENCE TO RELATED APPLICATION

This application claims priority to Provisional Application No. 62/523,179, filed Jun. 21, 2017, which is herein incorporated by reference in its entirety.

TECHNICAL FIELD

The present disclosure relates to medical systems and methods for mapping an anatomical space of the body. More specifically, the disclosure relates to systems and methods for cardiac mapping.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional three-dimensional (3D) mapping techniques include contact mapping and non-contact mapping, and may employ a combination of contact and non-contact mapping. In both techniques, one or more catheters are advanced into the heart. With some catheters, once in the chamber, the catheter may be deployed to assume a 3D shape. In contact mapping, physiological signals resulting from the electrical activity of the heart are acquired with one or more electrodes located at the catheter distal tip after determining that the tip is in stable and steady contact with the endocardium surface of a particular heart chamber. In non-contact-based mapping systems, using the signals detected by the non-contact electrodes and information on chamber anatomy and relative electrode location, the system provides physiological information regarding the endocardium of the heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm.

Various types of three-dimensional electroanatomical maps are known in the art. These include voltage maps, activation maps, and fractionation maps. There is an ongoing need to provide additional mapping technologies to improve the clinician's ability to identify and treat arrythmogenic tissue.

SUMMARY

This disclosure provides design, material, manufacturing method, and use alternatives for medical devices.

An example method for displaying physiological mapping data includes acquiring, at a plurality of signal-acquiring times, a plurality of electrogram signals of a body chamber using one or more electrodes disposed on a distal end of a catheter shaft at a plurality of anatomical locations within the body chamber, each electrogram signal relating to three-dimensional positional data corresponding to the plurality of anatomical locations for each of the plurality of electrodes.

Alternatively or additionally to any of the examples above, storing, in memory, the plurality of electrogram signals of the body chamber corresponding to electrical activities sensed at the one or more electrodes at corresponding anatomical locations at the plurality of signal-acquiring times.

Alternatively or additionally to any of the examples above, calculating, based on each of the plurality of electrogram signals of the body chamber, an activation recovery interval associated with each of the corresponding anatomical locations.

Alternatively or additionally to any of the examples above, determining, for each corresponding anatomical location, spatial gradient data of the activation recovery interval based on a distance between at least two neighboring anatomical locations.

Alternatively or additionally to any of the examples above, displaying a three-dimensional graphical representation of the spatial gradient data of the activation recovery interval between the at least two neighboring anatomical locations on a display device.

Alternatively or additionally to any of the examples above, determining the spatial gradient data of the activation recovery interval includes calculating, for each corresponding anatomical location, a derivative of the activation recovery interval with respect to a change in the distance between the at least two neighboring anatomical locations based on the plurality of signal-acquiring times.

Alternatively or additionally to any of the examples above, calculating the activation recovery interval includes determining an activation time and a recovery time for each corresponding anatomical location based on the plurality of electrogram signals with respect to the plurality of signal-acquiring times, and calculating the activation recovery interval based on a difference between the activation time and the recovery time for each corresponding anatomical location.

Alternatively or additionally to any of the examples above, calculating the activation recovery interval includes performing at least one of spatial smoothing and temporal smoothing of the activation recovery interval between the at least two neighboring anatomical locations for providing a gradual change of the activation recovery interval on the display device.

Alternatively or additionally to any of the examples above, displaying the three-dimensional graphical representation of the spatial gradient data of the activation recovery interval includes selectively displaying a region associated with the spatial gradient data satisfying a predetermined selection standard.

Alternatively or additionally to any of the examples above, selectively displaying the region associated with the spatial gradient data includes displaying the region exhibiting at least one predetermined characteristic of the spatial gradient data of the activation recovery interval between the at least two neighboring anatomical locations.

Alternatively or additionally to any of the examples above, selectively displaying the region associated with the spatial gradient data includes identifying, for display, the region representing a rate of change in the spatial gradient data that is greater than a predetermined threshold between the at least two neighboring anatomical locations.

Alternatively or additionally to any of the examples above, selectively displaying the region associated with the spatial gradient data includes identifying, for display, the region that is out of phase with respect to the activation recovery interval by a predetermined threshold between the at least two neighboring anatomical locations.

Another example method for displaying physiological mapping data includes acquiring, at a plurality of signal-acquiring times at a first pacing rate of a heart, a first plurality of electrogram signals of a body chamber using one or more electrodes disposed on a distal end of a catheter shaft at a plurality of anatomical locations within the body chamber, each first electrogram signal relating to three-dimensional positional data corresponding to the plurality of anatomical locations for each of the plurality of electrodes.

Alternatively or additionally to any of the examples above, storing, in memory, the first plurality of electrogram signals of the body chamber corresponding to electrical activities sensed at the one or more electrodes at corresponding anatomical locations at the plurality of signal-acquiring times at the first pacing rate.

Alternatively or additionally to any of the examples above, calculating, based on each of the first plurality of electrogram signals of the body chamber, a first activation recovery interval associated with each of the corresponding anatomical locations at the first pacing rate.

Alternatively or additionally to any of the examples above, acquiring, at the plurality of signal-acquiring times at a second pacing rate of the heart that is faster than the first pacing rate, a second plurality of electrogram signals of the body chamber using the one or more electrodes at the plurality of anatomical locations within the body chamber, each second electrogram signal relating to the three-dimensional positional data corresponding to the plurality of anatomical locations for each of the plurality of electrodes.

Alternatively or additionally to any of the examples above, storing, in memory, the second plurality of electrogram signals of the body chamber corresponding to the electrical activities sensed at the one or more electrodes at the corresponding anatomical locations at the plurality of signal-acquiring times at the second pacing rate.

Alternatively or additionally to any of the examples above, calculating, based on each of the second plurality of electrogram signals of the body chamber, a second activation recovery interval associated with each of the corresponding anatomical locations at the second pacing rate.

Alternatively or additionally to any of the examples above, determining, for each corresponding anatomical location, modulation data relating to repolarization rates based on the first and second activation recovery intervals with respect to a cycle length difference between the first and second pacing rates.

Alternatively or additionally to any of the examples above, displaying a three-dimensional graphical representation of the modulation data of the first and second activation recovery intervals between the first and second pacing rates on a display device.

Alternatively or additionally to any of the examples above, determining the modulation data relating to the repolarization rates based on the first and second activation recovery intervals includes calculating, for each corresponding anatomical location, a derivative of the activation recovery interval with respect to a change in the cycle length difference between the first and second pacing rates based on the plurality of signal-acquiring times.

Alternatively or additionally to any of the examples above, calculating each of the first and second activation recovery intervals includes determining an activation time and a recovery time for each corresponding anatomical location based on a corresponding plurality of electrogram signals with respect to corresponding signal-acquiring times, and calculating each activation recovery interval based on a difference between the activation time and the recovery time for each corresponding anatomical location.

Alternatively or additionally to any of the examples above, calculating each of the first and second activation recovery intervals includes performing at least one of spatial smoothing and temporal smoothing of the activation recovery interval between at least two neighboring anatomical locations for providing a gradual change of the activation recovery interval on the display device.

Alternatively or additionally to any of the examples above, displaying the three-dimensional graphical representation of the modulation data of the first and second activation recovery intervals includes selectively displaying a region associated with the modulation data satisfying a predetermined selection standard.

Alternatively or additionally to any of the examples above, selectively displaying the region associated with the modulation data includes displaying the region exhibiting at least one predetermined characteristic of the modulation data between the first and second activation recovery intervals at one or more of the anatomical locations.

Alternatively or additionally to any of the examples above, selectively displaying the region associated with the modulation data includes identifying, for display, the region representing a first rate of change that is less than a predetermined threshold in the repolarization rates between the first and second activation recovery intervals; and calculating a second rate of change between the first and second pacing rates.

Alternatively or additionally to any of the examples above, identifying the region representing the rate of change in the repolarization rates includes comparing the first rate of change with the second rate of change and identifying the region representing an inadequate repolarization rate at the one or more of the anatomical locations based on the comparison of the first and second rates of change.

An example system for cardiac mapping includes a catheter shaft with one or more electrodes coupled to a distal end of the catheter shaft, the one or more electrodes being configured to sense electrical signals at a plurality of anatomical locations within a heart.

Alternatively or additionally to any of the examples above, the system includes a processor coupled to the catheter shaft. The processor is configured to acquire, at a plurality of signal-acquiring times, a plurality of electrogram signals of the heart using the one or more electrodes at the plurality of anatomical locations, each electrogram signal relating to three-dimensional positional data corresponding to the plurality of anatomical locations for each of the plurality of electrodes. The processor is configured to store, in memory, the plurality of electrogram signals of the heart corresponding to electrical activities sensed at the one or more electrodes at corresponding anatomical locations at the plurality of signal-acquiring times. The processor is configured to calculate, based on each of the plurality of electrogram signals of the heart, an activation recovery interval associated with each of the corresponding anatomical locations. The processor is configured to determine, for each corresponding anatomical location, spatial gradient data of the activation recovery interval based on a distance between at least two neighboring anatomical locations.

Alternatively or additionally to any of the examples above, the system includes a display device coupled to the processor and configured to display a three-dimensional graphical representation of the spatial gradient data of the activation recovery interval between the at least two neighboring anatomical locations on the display device.

Alternatively or additionally to any of the examples above, the processor is further configured to calculate, for each corresponding anatomical location, a derivative of the activation recovery interval with respect to a change in the distance between the at least two neighboring anatomical locations based on the plurality of signal-acquiring times.

Alternatively or additionally to any of the examples above, the processor is further configured to determine an activation time and a recovery time for each corresponding anatomical location based on the plurality of electrogram signals with respect to the plurality of signal-acquiring times, and calculate the activation recovery interval based on a difference between the activation time and the recovery time for each corresponding anatomical location.

Alternatively or additionally to any of the examples above, the processor is further configured to perform at least one of spatial smoothing and temporal smoothing of the activation recovery interval between the at least two neighboring anatomical locations for providing a gradual change of the activation recovery interval on the display device.

Alternatively or additionally to any of the examples above, the processor is further configured to selectively display a region associated with the spatial gradient data satisfying a predetermined selection standard on the display device.

Alternatively or additionally to any of the examples above, the processor is further configured to display the region exhibiting at least one predetermined characteristic of the spatial gradient data of the activation recovery interval between the at least two neighboring anatomical locations.

Alternatively or additionally to any of the examples above, the processor is further configured to identify, for display, the region representing a rate of change in the spatial gradient data that is greater than a predetermined threshold between the at least two neighboring anatomical locations.

Alternatively or additionally to any of the examples above, the processor is further configured to identify, for display, the region that is out of phase with respect to the activation recovery interval by a predetermined threshold between the at least two neighboring anatomical locations.

An another system for cardiac mapping includes a catheter shaft with one or more electrodes coupled to a distal end of the catheter shaft, the one or more electrodes being configured to sense electrical signals at a plurality of anatomical locations within a heart.

Alternatively or additionally to any of the examples above, the system includes a processor coupled to the catheter shaft. The processor is configured to acquire, at a plurality of signal-acquiring times at a first pacing rate of the heart, a first plurality of electrogram signals of the heart using the one or more electrodes, each first electrogram signal relating to three-dimensional positional data corresponding to the plurality of anatomical locations for each of the plurality of electrodes. The processor is configured to store, in memory, the first plurality of electrogram signals of the heart corresponding to electrical activities sensed at the one or more electrodes at corresponding anatomical locations at the plurality of signal-acquiring times at the first pacing rate. The processor is configured to calculate, based on each of the first plurality of electrogram signals of the heart, a first activation recovery interval associated with each of the corresponding anatomical locations at the first pacing rate. The processor is configured to acquire, at the plurality of signal-acquiring times at a second pacing rate of the heart that is faster than the first pacing rate, a second plurality of electrogram signals of the heart using the one or more electrodes, each second electrogram signal relating to the three-dimensional positional data corresponding to the plurality of anatomical locations for each of the plurality of electrodes. The processor is configured to store, in memory, the second plurality of electrogram signals of the heart corresponding to the electrical activities sensed at the one or more electrodes at the corresponding anatomical locations at the plurality of signal-acquiring times at the second pacing rate. The processor is configured to calculate, based on each of the second plurality of electrogram signals of the heart, a second activation recovery interval associated with each of the corresponding anatomical locations at the second pacing rate. The processor is configured to determine, for each corresponding anatomical location, modulation data relating to repolarization rates based on the first and second activation recovery intervals with respect to a cycle length difference between the first and second pacing rates.

Alternatively or additionally to any of the examples above, the system also includes a display device coupled to the processor and configured to display a three-dimensional graphical representation of the modulation data of the first and second activation recovery intervals between the first and second pacing rates on the display device.

Alternatively or additionally to any of the examples above, the processor is further configured to calculate, for each corresponding anatomical location, a derivative of the activation recovery interval with respect to a change in the cycle length difference between the first and second pacing rates based on the plurality of signal-acquiring times.

Alternatively or additionally to any of the examples above, the processor is further configured to determine an activation time and a recovery time for each corresponding anatomical location based on a corresponding plurality of electrogram signals with respect to corresponding signal-acquiring times, and calculate each activation recovery interval based on a difference between the activation time and the recovery time for each corresponding anatomical location.

Alternatively or additionally to any of the examples above, the processor is further configured to perform at least one of spatial smoothing and temporal smoothing of the activation recovery interval between at least two neighboring anatomical locations for providing a gradual change of the activation recovery interval on the display device.

Alternatively or additionally to any of the examples above, the processor is further configured to selectively display a region associated with the modulation data satisfying a predetermined selection standard.

Alternatively or additionally to any of the examples above, the processor is further configured to display the region exhibiting at least one predetermined characteristic of the modulation data between the first and second activation recovery intervals at one or more of the anatomical locations.

Alternatively or additionally to any of the examples above, the processor is further configured to identify, for display, the region representing a first rate of change that is less than a predetermined threshold in the repolarization rates between the first and second activation recovery intervals; and calculate a second rate of change between the first and second pacing rates.

Alternatively or additionally to any of the examples above, the processor is further configured to compare the first rate of change with the second rate of change and identify the region representing an inadequate repolarization rate at the one or more of the anatomical locations based on the comparison of the first and second rates of change.

The above summary of some embodiments is not intended to describe each disclosed embodiment or every implementation of the present disclosure. The Figures, and Detailed Description, which follow, more particularly exemplify these embodiments.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

The disclosure may be more completely understood in consideration of the following detailed description in connection with the accompanying drawings, in which.

Figure 1:
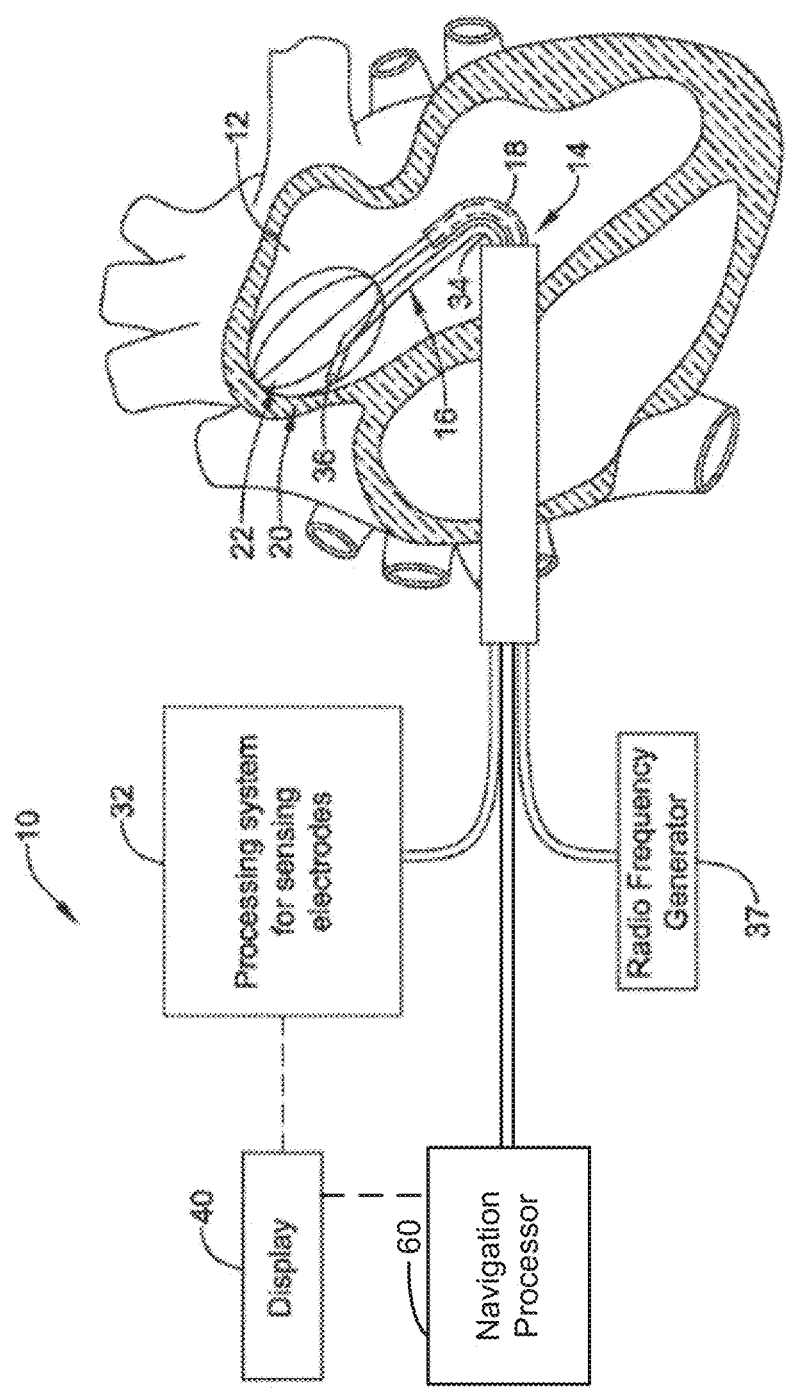
FIG. 1 is a schematic block diagram depicting an illustrative navigation system in accordance with embodiments of the disclosed subject matter.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an example", "some examples", "other examples", etc., indicate that the example described may include one or more particular features, structures, and/or characteristics. However, such recitations do not necessarily mean that all examples include the particular features, structures, and/or characteristics. Additionally, when particular features, structures, and/or characteristics are described in connection with one example, it should be understood that such features, structures, and/or characteristics may also be used in connection with other examples whether or not explicitly described unless clearly stated to the contrary. Also, when particular features, structures, and/or characteristics are described in connection with one example, it is implicit that other examples may include less than all of the disclosed features, structures, and/or characteristics in all combinations.

The following detailed description should be read with reference to the drawings in which similar elements in different drawings are numbered the same. The drawings, which are not necessarily to scale, depict illustrative embodiments and are not intended to limit the scope of the disclosure.

Mapping the electrophysiology of heart rhythm disorders often involves the introduction of a basket catheter (e.g. the ORION catheter marketed by Boston Scientific Corporation) or other mapping/sensing device having a plurality of sensors into a cardiac chamber. The sensors, e.g., electrodes, detect physiological signals, such as cardiac electrical activity, at sensor locations. It may be desirable to have detected cardiac electrical activity processed into electrogram signals that accurately represent cellular excitation through cardiac tissue relative to the sensor locations. A processing system may then analyze and output the signal to a display device. Further, the processing system may output the signal as processed output, such as a static or dynamic activation map. A user, such as a physician, may use the processed output to perform a diagnostic procedure.

FIG. 1 is a schematic view of a system 10 for accessing a targeted tissue region in the body for diagnostic and/or therapeutic purposes. FIG. 1 generally shows the system 10 deployed in the left atrium of the heart. Alternatively, system 10 can be deployed in other regions of the heart, such as the left ventricle, right atrium, or right ventricle.

The system 10 includes a mapping catheter or probe 14 and an ablation catheter or probe 16. Each probe 14/16 may be separately introduced into the selected heart region 12 through a vein or artery (e.g., the femoral vein or artery) using a suitable percutaneous access technique. Alternatively, the mapping probe 14 and the ablation probe 16 can be assembled in an integrated structure for simultaneous introduction and deployment in the heart region 12.

The mapping probe 14 generally includes a flexible catheter body 18 carrying, at its distal end, a three-dimensional multiple electrode structure 20. In the illustrated embodiment, the structure 20 takes the form of a basket defining an open interior space 22 (see FIG. 2), although other multiple electrode structures could be used. The structure 20 carries a plurality of mapping electrodes 24 (not explicitly shown on FIG. 1, but shown on FIG. 2) each having an electrode location on the structure 20. Each electrode 24 may be configured to sense or detect intrinsic physiological activity, for example represented as electrical signals, in an anatomical region adjacent to each electrode 24.

In addition, the electrodes 24 may be configured to detect activation signals of the intrinsic physiological activity within the anatomical structure. For example, intrinsic cardiac electrical activity may include repeating or semi-repeating waves of electrical activity with relatively large spikes in activity at the beginning of activation events. The electrodes 24 may sense such activation events and the times at which such activation events occur. Generally, the electrodes 24 may sense activation events at different times as an electrical activity wave propagates through the heart. For instance, an electrical wave may begin near a first group of electrodes 24, which may sense an activation event at relatively the same time or within a relatively small window of time. As the electrical wave propagates through the heart, a second group of electrodes 24 may sense the activation event of the electrical wave at times later than the first group of electrodes 24.

The electrodes 24 are electrically coupled to a processing system 32. A signal wire (not shown) may be electrically coupled to each electrode 24 on structure 20. The signal wires may extend through the body 18 of the probe 14 and electrically couple each electrode 24 to an input of the processing system 32. The electrodes 24 sense cardiac electrical activity in the anatomical region, e.g., myocardial tissue, adjacent to their physical location within the heart. The sensed cardiac electrical activity (e.g., electrical signals generated by the heart which may include activation signals) may be processed by the processing system 32 to assist a user, for example a physician, by generating processed output—e.g. an anatomical map (e.g., a vector field map, an activation time map) or a Hilbert transform diagram—to identify one or more sites within the heart appropriate for a diagnostic and/or treatment procedure, such as an ablation procedure. For example, the processing system 32 may identify a near-field signal component (e.g., activation signals originating from cellular tissue adjacent to the mapping electrodes 24) or an obstructive far-field signal component (e.g., activation signals originating from non-adjacent tissue). In such examples where the structure 20 is disposed in an atrium of the heart, as in FIG. 1, the near-field signal component may include activation signals originating from atrial myocardial tissue whereas the far-field signal component may include activation signals originating from ventricular myocardial tissue. The near-field activation signal component may be further analyzed to find the presence of a pathology and to determine a location suitable for ablation for treatment of the pathology (e.g., ablation therapy).

The processing system 32 may include dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired physiological activity. In some examples, the processing system 32 includes a general purpose microprocessor and/or a specialized microprocessor (e.g., a digital signal processor, or DSP, which may be optimized for processing activation signals) that executes instructions to receive, analyze and display information associated with the received physiological activity. In such examples, the processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that processing system 32 can take any suitable form for receiving electrical signals and processing the received electrical signals.

In addition, the processing system 32 may be configured to measure the sensed cardiac electrical activity in the myocardial tissue adjacent to the electrodes 24. For example, the processing system 32 may be configured to detect cardiac electrical activity associated with a dominant rotor or divergent activation pattern in the anatomical feature being mapped. Dominant rotors and/or divergent activation patterns may have a role in the initiation and maintenance of atrial fibrillation, and ablation of the rotor path, rotor core, and/or divergent foci may be effective in terminating the atrial fibrillation. The processing system 32 processes the sensed cardiac electrical activity to generate a display of relevant characteristics. Such processed output may include isochronal maps, activation time maps, phase maps, action potential duration (APD) maps, Hilbert transform diagrams, vector field maps, contour maps, reliability maps, electrograms, cardiac action potentials and the like. The relevant characteristics may assist a user to identify a site suitable for ablation therapy.

The ablation probe 16 includes a flexible catheter body 34 that carries one or more ablation electrodes 36. The one or more ablation electrodes 36 are electrically connected to an radio frequency (RF) generator 37 that is configured to deliver ablation energy to the one or more ablation electrodes 36. The ablation probe 16 may be movable with respect to the anatomical feature to be treated, as well as the structure 20 of the mapping probe 14. The ablation probe 16 may be positionable between or adjacent to the electrodes 24 of the structure 20 as the one or more ablation electrodes 36 are positioned with respect to the tissue to be treated.

The processing system 32 may output data to a suitable device, for example the display device 40, which may display relevant information for a user. In some examples, the device 40 is a CRT, LED, or other type of display, or a printer. The device 40 presents the relevant characteristics in a format useful to the user.

In addition, the mapping probe 14 is operatively coupled to a navigation processor 60 that is configured to track the position of the structure 20 and its components within a pre-determined space, and to generate position-identifying output for display on device 40 that aids the user in guiding the mapping probe 14 and/or the ablation electrode(s) 36 into contact with tissue at the site identified for ablation.

It is emphasized that in some embodiments the system 10 does not include the ablation probe 16. That is, the mapping probe 14 and associated hardware and software (e.g., the processing system 32 and the display 40) can be utilized as a stand-alone electroanatomical mapping system independent of the ablation probe 16 and corresponding hardware and software. In one particular embodiment, the mapping probe 14, the processing system 32, the display 40 and the navigation processor 50 are components of the RHYTHMIA™ mapping system marketed by Boston Scientific Corporation.

Figure 2:
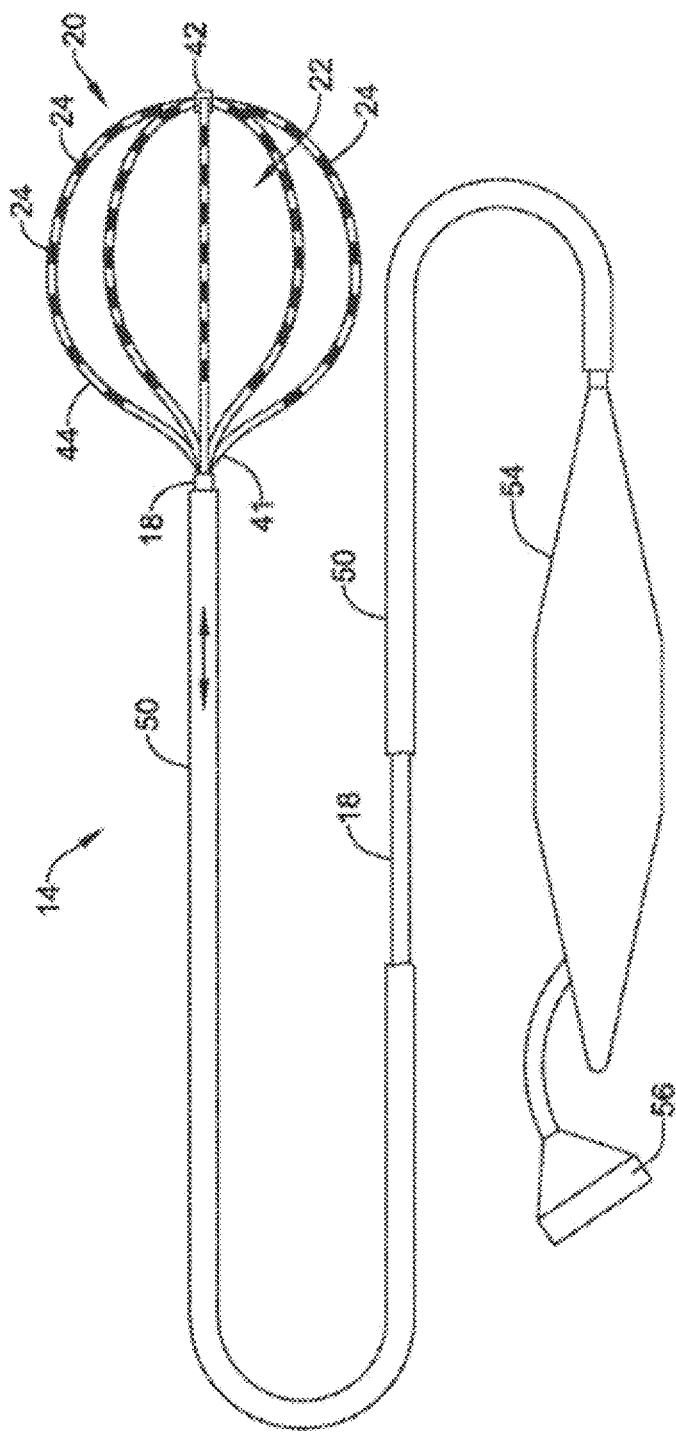
FIG. 2 is a schematic block diagram depicting an illustrative computing device in accordance with embodiments of the disclosed subject matter.

FIG. 2 illustrates the mapping catheter 14 and the shows the electrodes 24 at the distal end suitable for use in the system 10 shown in FIG. 1. As shown, the illustrated three-dimensional multiple electrode structure 20 includes a base member 41 and an end portion 42 between which flexible splines 44 generally extend in a circumferentially spaced relationship. As discussed herein, the structure 20 may take the form of a basket defining an open interior space 22. In some examples, the splines 44 are made of a resilient inert material, such as Nitinol, other metals, silicone rubber, suitable polymers, or the like and are connected between the base member 41 and the end portion 42 in a resilient, pretensioned condition, to bend and conform to the tissue surface they contact. In the example illustrated in FIG. 2, eight splines 44 form the three-dimensional multiple electrode structure 20. Additional or fewer splines 44 could be used in other examples. As illustrated, each spline 44 carries eight mapping electrodes 24. Additional or fewer mapping electrodes 24 could be disposed on each spline 44 in other examples of three-dimensional multiple electrode structure 20. In the example illustrated in FIG. 2, the structure 20 is relatively small (e.g., 40 mm or less in diameter). In alternative examples, the structure 20 is even smaller or larger (e.g., less than or greater than 40 mm in diameter).

A slidable sheath 50 may be movable along the major axis of catheter body 18. Moving the sheath 50 distally relative to the catheter body 18 may cause the sheath 50 to move over the structure 20, thereby collapsing structure 20 into a compact, low profile condition suitable for introduction into and/or removal from an interior space of an anatomical structure, such as, for example, the heart. In contrast, moving the sheath 50 proximally relative to the catheter body may expose the structure 20, allowing the structure 20 to elastically expand and assume the pretensioned position illustrated in FIG. 2. Alternatively, in some embodiments, the structure 20 may be extendable and retractable relative to the sheath 50 (by means of a control mechanism operable by a user). In such embodiments, the structure 20 is withdrawn within the sheath 50 and thereby maintained in a collapsed configuration during advancement of the structure 20 through the patient's vasculature to the target cardiac region (e.g., the left atrium) and then extended from the sheath 50 so as to allow the structure 20 to assume its expanded configuration.

The signal wires (not shown) electrically coupled to the respective mapping electrodes 24 may extend through the body 18 of the mapping probe 14 (or otherwise through and/or along body 18) into a handle 54, in which they are coupled to an external connector 56, which may be a multiple pin connector. The connector 56 electrically couples the mapping electrodes 24 to the processing system 32. It should be understood that these descriptions are just examples.

In some embodiments, the mapping probe 14 may also include one or more navigation sensors (not shown) that provide an output to the navigation processor 60 (see FIG. 1) as part of a three-dimensional navigation system incorporated into the system 10. The navigation sensor, when present, can be comprised of any navigation sensor known in the art or later developed. In one embodiment, the navigation sensor may comprise a magnetic field sensor, whether now known or later developed, that generates an output in response to a three-dimensional electromagnetic field generated by one or more external field generators. In particular, the navigation sensor(s) may include sensors such as inductive sensing coils and/or various sensing elements such as magneto-resistive (MR) sensing elements (e.g., anisotropic magneto-resistive (AMR) sensing elements, giant magneto-resistive (GMR) sensing elements, tunneling magneto-resistive (TMR) sensing elements, Hall effect sensing elements, colossal magneto-resistive (CMR) sensing elements, extraordinary magneto-resistive (EMR) sensing elements, spin Hall sensing elements, and the like), giant magneto-impedance (GMI) sensing elements, and/or fluxgate sensing elements.

Some addition details regarding these and other example mapping systems and methods for processing signals generated by a mapping catheter can be found in U.S. Pat. Nos. 6,070,094, 6,233,491, and 6,735,465, the disclosures of which are hereby expressly incorporated herein by reference.

One particular example of the mapping probe 14 is the ORION™ high resolution mapping catheter marketed by Boston Scientific Corporation.

Figure 3:
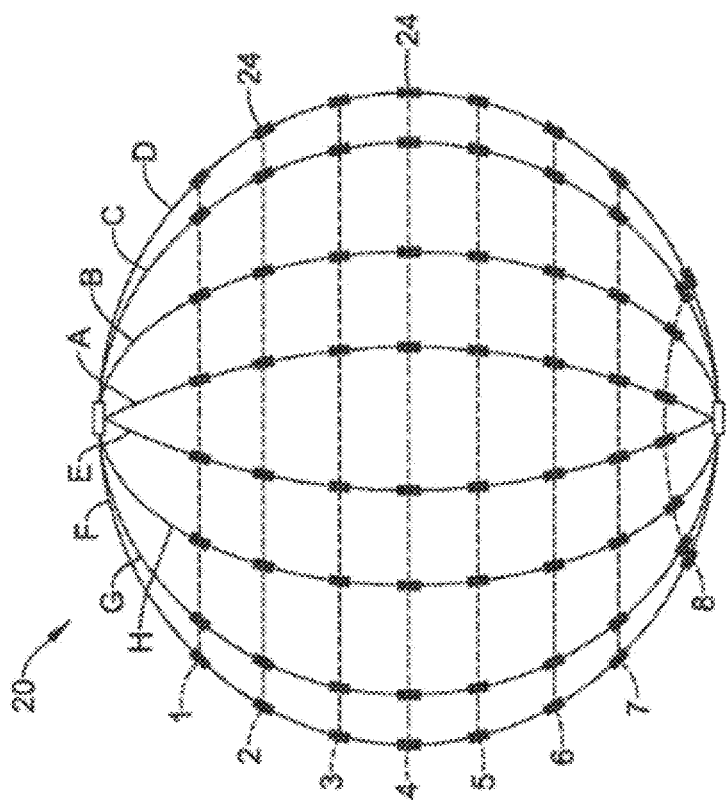
FIG. 3 is a schematic block diagram depicting a first exemplary repolarization mapping unit in accordance with embodiments of the disclosed subject matter.

To illustrate the operation of the system 10, FIG. 3 is a schematic side view of an example of the basket structure 20 including the plurality of mapping electrodes 24. In the illustrated example, the basket structure 20 includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H). While the arrangement of sixty-four mapping electrodes 24 is shown disposed on the basket structure 20, the mapping electrodes 24 may alternatively be arranged in different numbers (more or fewer splines and/or electrodes), on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated (e.g. left atrium, left ventricle, right atrium, or right ventricle of the heart), the processing system 32 may be configured to record the cardiac electrical activity from each electrode 24. Further, the recorded cardiac electrical activity may be related to the physiological activity of the adjacent anatomical structure. For instance, cardiac electrical activity sensed by the electrodes 24 may include activation signals which may indicate an onset of physiological activity (e.g. contraction of the heart). Further, cardiac electrical activity corresponding to physiological activity may be sensed in response to intrinsic physiological activity (e.g. intrinsically generated electrical signals) or based on a predetermined pacing protocol instituted by at least one of the plurality of electrodes 24 (e.g. delivered electrical signals delivered by a pacing device).

The electrodes 24 are configured to sense a change in the voltage potential of a propagating cellular activation wavefront. The change in voltage potential of cellular tissue may be sensed, collected and displayed as an electrogram. An electrogram may be a visual representation of the change in voltage potential of the cellular tissue over time. Additionally, it may be desirable to define a specific characteristic of an electrogram as a "fiducial" point of the electrical signal. For purposes of this disclosure, a fiducial point may be understood as a characteristic of an electrogram that can be utilized as an identifying characteristic of cellular activation. Fiducial points may correspond to the peak magnitude, change in slope, and/or deflection of the electrical signal. It is contemplated that fiducial points may include other characteristics of an electrogram or other signal used to generate diagnostic and/or processed output. Further, fiducial points may be identified manually by a clinician and/or automatically by processing system 32.

In various embodiments, the system 10 is configured to analyze a recovery of a particular region of a heart following activation for evaluating the recovery of the heart. It is known that the recovery of the heart is a property of each cardiac cell in the heart. Abnormal cellular tissues alter the recovery properties of the cells, and also alter global repolarization. In one example, a chamber that has been in chaotic activity for a period of time starts to develop changes in its recovery. In embodiments, the system 10 performs the activation recovery analysis of the heart by mapping regional recovery properties for identifying regions that may be instrumental in maintaining and sustaining abnormal conduction.

Figure 4:
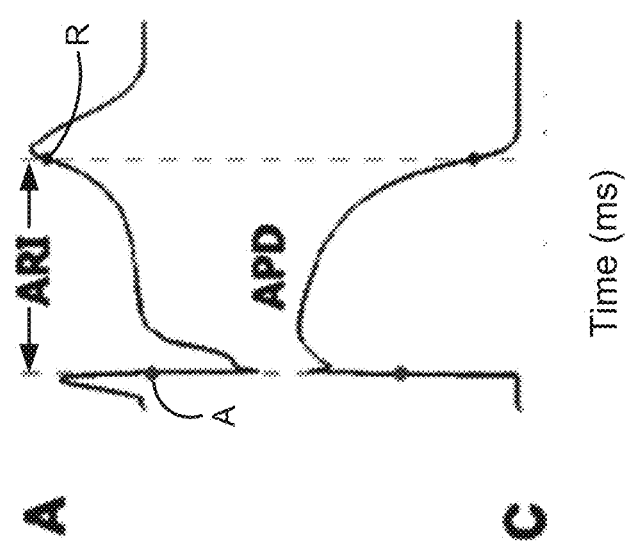
FIG. 4 is a schematic block diagram depicting a second exemplary repolarization mapping unit in accordance with embodiments of the disclosed subject matter.

In various embodiments, the system 10 is configured to determine an activation recovery interval (ARI) at a plurality of locations within a cardiac chamber of interest (e.g., the left atrium) corresponding to the known locations of the electrodes 24 on the mapping probe 14. Generally speaking, the ARI can be defined in two ways. In one aspect, the ARI can be defined as a time interval between the time of local activation and the time of repolarization (as determined based on a pre-selected T wave trigger, e.g., upstroke, maximum, downstroke, etc.) at a given location within the cardiac chamber. Alternatively, the ARI can be defined as a time interval between the time of repolarization (as determined per the above) and some other time reference other than the local activation time at a given location within the cardiac chamber. This can be seen in FIG. 4, illustrating a typical unipolar electrogram such as could be generated by a conventional cardiac mapping or recording system. As can be seen in FIG. 4, both the activation time 'A' and the repolarization time 'R' can be identified by analysis of the change in amplitude of the EGM signal over time. As further shown, the ARI in FIG. 4 corresponds to the time period between A and R.

Figure 5:
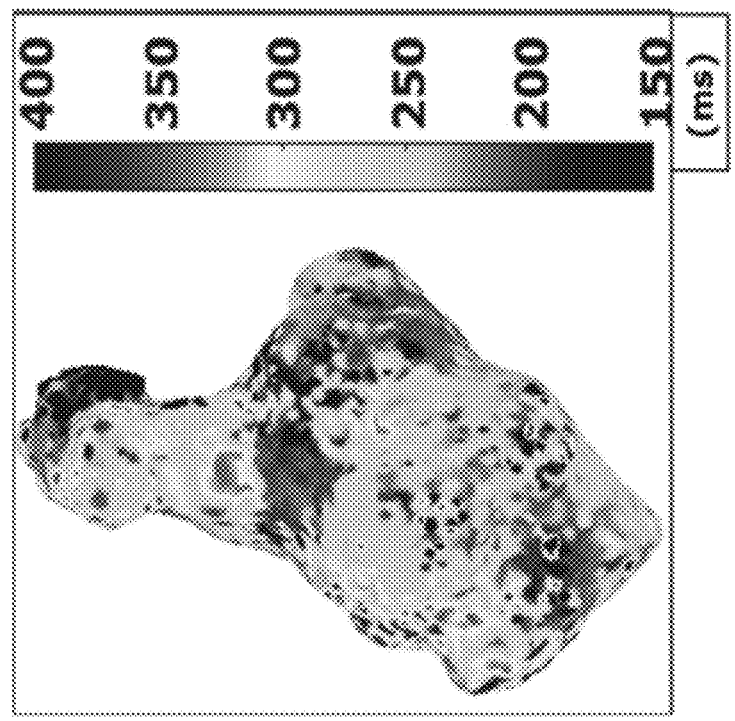
FIG. 5 is a flow diagram depicting an illustrative method of a first exemplary process of the repolarization mapping unit of FIG. 3 using an electromagnetic navigation system in accordance with embodiments of the disclosed subject matter.

The inventors of the present disclosure have determined that the system 10 can be utilized to provide the user with valuable visualization tools for analyzing the ARI associated with different locations within the cardiac chamber, and in doing so, assist the user in identifying arrhythmogenic cardiac tissue substrates. FIG. 5 illustrates a representative such visualization tool, in this case, a three-dimensional electroanatomic map of a cardiac chamber (in this case the left ventricle). Specifically, the map of FIG. 5 is a color-coded three-dimensional ARI map for the chamber, providing a graphical illustration of the ARI associated with each location within the chamber for a given cardiac cycle. Variations in ARI across the chamber can be analyzed to identify healthy and potentially arrhythmogenic tissue regions. In particular, large spatial gradients in the ARI (i.e., changes in the ARI over a given distance exceeding predetermined thresholds) can indicate the presence of arrythmogenic tissue. Similarly, when the user employs pacing, differences between changes in pacing rates and associated ARIs for a given tissue region can also provide an indication of unhealthy cardiac tissue.

Figure 6:
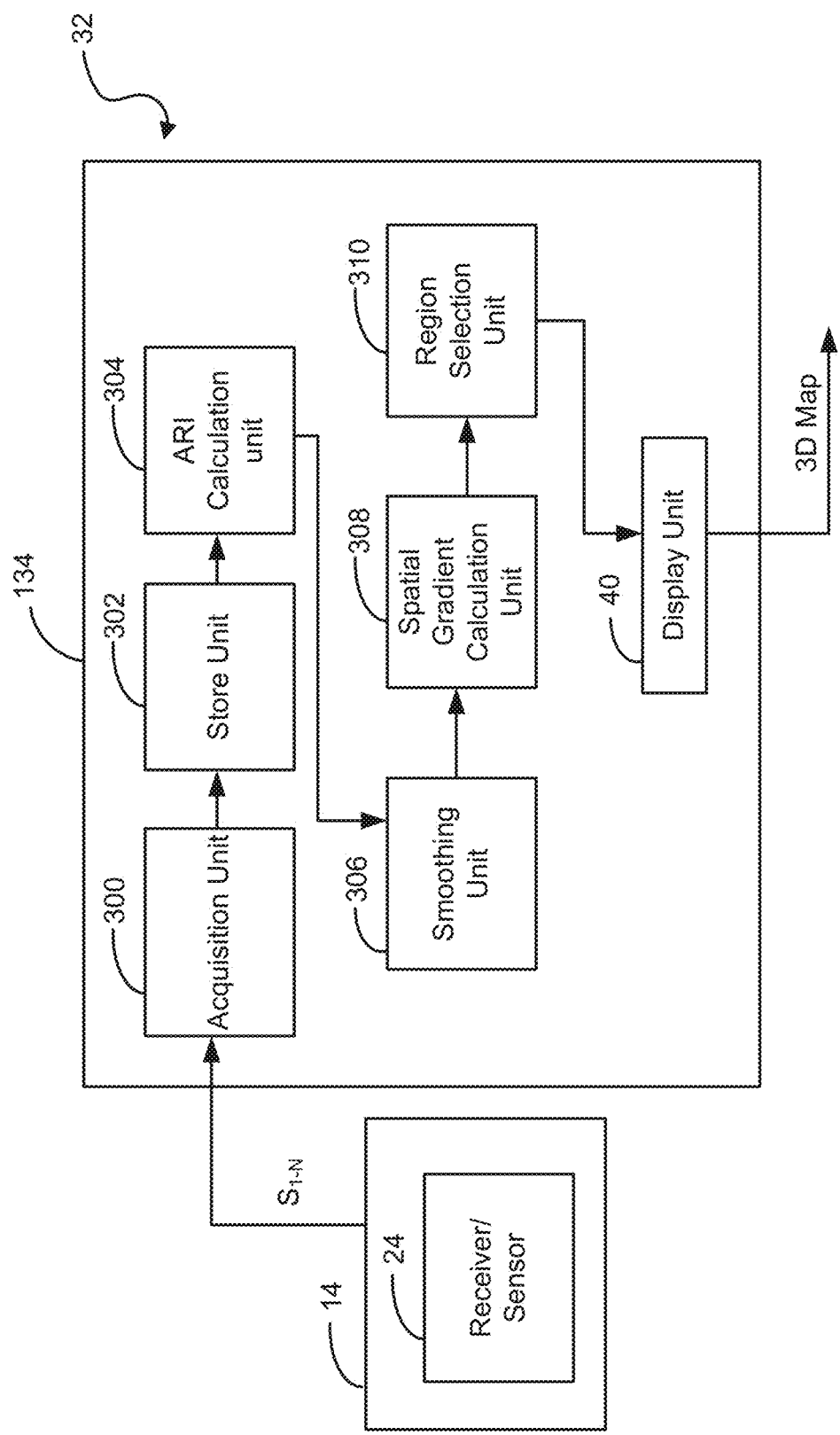
FIG. 6 is a flow diagram depicting an illustrative method of a second exemplary process of the repolarization mapping unit of FIG. 4 using an electromagnetic navigation system in accordance with embodiments of the disclosed subject matter.

FIG. 6 is a schematic block diagram depicting a portion of the system 10 including, as a component of the processing system 32, a first exemplary repolarization mapping unit 134 in accordance with embodiments of the disclosed subject matter. In embodiments, the mapping probe (or catheter shaft) 14 having the mapping electrodes 24 thereon sense electrical signals $S_{1-N}$ representing activation of adjacent cardiac tissue. In embodiments, the electrodes 24 are configured to sense the electrical signals $S_{1-N}$ at a plurality of anatomical locations within a heart.

In this example, the repolarization mapping unit 134 is communicatively coupled to the mapping probe 14, and includes an acquisition unit 300, a store unit 302, an ARI calculation unit 304, a smoothing unit 306, a spatial gradient calculation unit 308, a region selection unit 310, and a display unit 312. Although sub units in the repolarization mapping unit 134 are illustratively depicted as separate units, the functions and capabilities of each unit can be implemented, combined, and used in conjunction with/into any unit or any combination of units to suit different applications. Additionally, any number of these components, or combinations thereof, is distributed and/or duplicated across a number of computing devices.

In embodiments, the acquisition unit 300 is configured to acquire, at a plurality of signal-acquiring times, a plurality of electrogram signals, such as the electrical signals $S_{1-N}$, of the heart using the electrodes 24 at the plurality of anatomical locations. Each electrogram signal relates to three-dimensional positional data corresponding to the plurality of anatomical locations for each of the electrodes 24.

In embodiments, the store unit 302 is configured to store, in memory 230, the plurality of electrogram signals $S_{1-N}$ of the heart corresponding to electrical activities sensed at the electrodes 24 at corresponding anatomical locations at the plurality of signal-acquiring times. Based on each of the plurality of electrogram signals $S_{1-N}$ of the heart, an activation recovery interval (ARI) associated with each of the corresponding anatomical locations are calculated by the ARI calculation unit 304. Other data related to the repolarization mapping unit 134 is stored in memory 230 during operation to suit different applications.

In embodiments, the ARI calculation unit 304 estimates spatial recovery times of the heart from the recovery component of each spatial electrogram, such as the local T-wave of EGM complex representing the local repolarization (or recovery) of the local ventricular tissue of the heart, by calculating a first time derivative. For example, a delta value representing a difference between the recovery and the activation is calculated for each spatial electrogram to calculate the ARI that represents local repolarization properties. In one embodiment, the ARI calculation unit 304 determines an activation time and a recovery time for each corresponding anatomical location based on the plurality of electrogram signals $S_{1-N}$ with respect to the plurality of signal-acquiring times, and calculate the activation recovery interval based on a difference between the activation time and the recovery time for each corresponding anatomical location.

In embodiments, the ARI can be calculated for each of anatomical location on the tissue surface of the heart for which electroanatomic data corresponding to the electrograms is available. Calculated ARIs are compared between anatomical regions of the heart to derive spatial estimates of the dispersion of ARIs as an indication of underlying disease. A difference between ARIs for the regions provides an indication of the dispersion of the ARIs. Subsequently, the ARIs are displayed by the display unit 312 in the form of a spatial three-dimensional (3D) map on the display device 270. In embodiments, the display device 270 is coupled to the processor 220 and is configured to display a three-dimensional graphical representation of the spatial gradient data of the ARI between the at least two neighboring anatomical locations using the display unit 312.

In embodiments, the smoothing unit 306 is configured to perform at least one of spatial smoothing and temporal smoothing of the ARI between at least two neighboring anatomical locations for providing a gradual change of the activation recovery interval on the display device 270. In one example, a sharp depth change in edges of an image associated with the 3D ARI map can be spatially and temporally smoothed to generate an improved 3D ARI map enabling a viewer to feel more comfortable to review.

In embodiments, the spatial gradient calculation unit 308 is configured to determine, for each corresponding anatomical location, spatial gradient data of the ARI based on a distance between at least two neighboring anatomical locations. In one example, the spatial gradient calculation unit 308 calculates, for each corresponding anatomical location, a derivative of the activation recovery interval with respect to a change in the distance between the at least two neighboring anatomical locations based on the plurality of signal-acquiring times.

In embodiments, the region selection unit 310 is configured to selectively display a region associated with the spatial gradient data satisfying a predetermined selection standard on the display device 270. In one example, the selection standard refers to selecting, for display, the region exhibiting at least one predetermined characteristic of the spatial gradient data of the activation recovery interval between the at least two neighboring anatomical locations. In another example, the region selection unit 310 is configured to identify, for display, the region representing a rate of change in the spatial gradient data that is greater than a predetermined threshold between the at least two neighboring anatomical locations.

In yet another example, the region selection unit 310 is configured to identify, for display, the region that is out of phase with respect to the ARI by a predetermined threshold between the at least two neighboring anatomical locations. For example, the identified regions can be highlighted in various colors to indicate variants with respect to time (e.g., milliseconds). For example, a blue region represents a faster recovery time in the range of 150 to 200 milliseconds indicating normally functioning tissues of the heart, or a red region represents a slower recovery time in the range of 350 to 400 milliseconds indicating abnormally functioning tissues of the heart. Other suitable highlighting methods are also contemplated to suit different applications.

Figure 7:
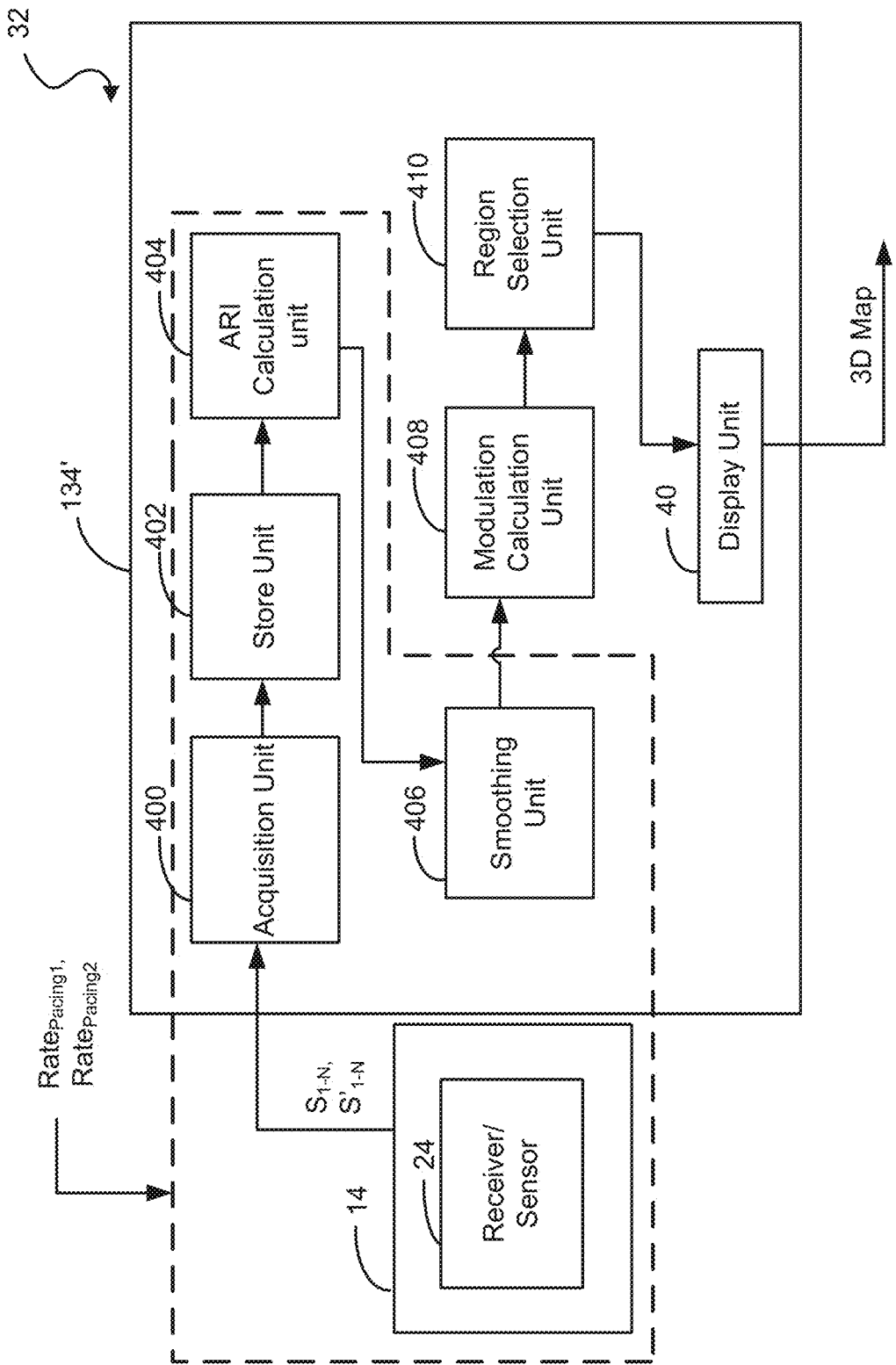
FIG. 7 is a schematic block diagram depicting a second exemplary repolarization mapping unit, in accordance with embodiments of the disclosed subject matter.

FIG. 7 is a schematic block diagram depicting a second exemplary repolarization mapping unit 134' in accordance with embodiments of the disclosed subject matter. In this example, components shared with the repolarization mapping unit 134' have identical reference numbers. As discussed above, the mapping probe 14 having the mapping electrodes 24 senses electrical signals from adjacent cardiac tissue.

In this example, the repolarization mapping unit 134' is communicatively coupled to the mapping probe 14, and includes an acquisition unit 400, a store unit 402, an ARI calculation unit 404, a smoothing unit 406, a spatial gradient calculation unit 408, a region selection unit 410, and a display unit 412. Although sub units in the repolarization mapping unit 134' are illustratively depicted as separate units, the functions and capabilities of each unit can be implemented, combined, and used in conjunction with/into any unit or any combination of units to suit different applications. Additionally, any number of these components, or combinations thereof, is distributed and/or duplicated across a number of computing devices.

In the embodiment of FIG. 7, a pacing-induced arrhythmia is induced at different pacing rates, a common procedure for electrophysiology studies. In short, a pacing stimuli is applied to the heart at two or more pacing rate using, e.g., the mapping probe 14, the ablation probe 16 (when present) or some other device not shown in FIG. 1 (e.g., a temporary pacing system utilizing a temporary endocardial lead, as is known in the art). In embodiments, the acquisition unit 400 is configured to acquire, at a plurality of signal-acquiring times at a first pacing rate $Rate_{Pacing1}$ of the heart, a first plurality of electrogram signals, such as the electrical signals $S_{1-N}$, of the heart using the electrodes 24. Each first electrogram signal is related to three-dimensional positional data corresponding to the plurality of anatomical locations for each of the electrodes 24. One aspect of the acquisition unit 400 is that it acquires again, at the plurality of signal-acquiring times at a second pacing rate $Rate_{Pacing2}$ of the heart that is faster than the first pacing rate $Rate_{Pacing1}$, a second plurality of electrogram signals $S'_{1-N}$ of the heart using the electrodes 24. As with the first electrogram signal, each second electrogram signal is related to the three-dimensional positional data corresponding to the plurality of anatomical locations for each of the electrodes 24.

In embodiments, the store unit 402 is configured to store, in memory 230, the first plurality of electrogram signals $S_{1-N}$ of the heart corresponding to electrical activities sensed at the electrodes 24 at corresponding anatomical locations at the plurality of signal-acquiring times at the first pacing rate $Rate_{Pacing1}$. Another aspect of the store unit 402 is that it stores again, in memory 230, the second plurality of electrogram signals $S'_{1-N}$ of the heart corresponding to the electrical activities sensed at the electrodes 24 at the corresponding anatomical locations at the plurality of signal-acquiring times at the second pacing rate $Rate_{Pacing2}$.

In embodiments, the ARI calculation unit 404 is configured to calculate, based on each of the first plurality of electrogram signals $S_{1-N}$ of the heart, a first activation recovery interval associated with each of the corresponding anatomical locations at the first pacing rate $Rate_{Pacing1}$. As with the units 400, 402, the ARI calculation unit 404 calculate again, based on each of the second plurality of electrogram signals $S'_{1-N}$ of the heart, a second activation recovery interval associated with each of the corresponding anatomical locations at the second pacing rate $Rate_{Pacing2}$. In one embodiment, the ARI calculation unit 404 determines an activation time and a recovery time for each corresponding anatomical location based on a corresponding plurality of electrogram signals $S_{1-N}$, $S'_{1-N}$ with respect to corresponding signal-acquiring times, and calculate each activation recovery interval based on a difference between the activation time and the recovery time for each corresponding anatomical location.

In embodiments, the smoothing unit 406 is configured to perform at least one of spatial smoothing and temporal smoothing of the ARI between at least two neighboring anatomical locations for providing a gradual change of the activation recovery interval on the display device 270. In embodiments, the modulation calculation unit 408 is configured to determine, for each corresponding anatomical location, modulation data relating to repolarization rates based on the first and second ARIs with respect to a cycle length difference between the first and second pacing rates $Rate_{Pacing1}$, $Rate_{Pacing2}$. In one embodiment, the modulation data refers to information associated with a difference between the first and second ARIs with respect to the cycle length difference. In one example, the modulation calculation unit 408 calculates, for each corresponding anatomical location, a derivative of the activation recovery interval with respect to a change in the cycle length difference between the first and second pacing rates $Rate_{Pacing1}$, $Rate_{Pacing2}$ based on the plurality of signal-acquiring times.

In embodiments, the display device 270 is coupled to the processor 220 and is configured to display a three-dimensional graphical representation of the modulation data of the first and second ARIs between the first and second pacing rates $Rate_{Pacing1}$, $Rate_{Pacing2}$ using the display unit 412. In embodiments, the region selection unit 410 is configured to selectively display a region associated with the modulation data satisfying a predetermined selection standard. In one example, the selection standard refers to selecting, for display, the region exhibiting at least one predetermined characteristic of the modulation data between the first and second ARIs at one or more of the anatomical locations.

In another example, the region selection unit 410 is configured to identify, for display, the region representing a first rate of change that is less than a predetermined threshold in the repolarization rates between the first and second ARIs, and calculate a second rate of change between the first and second pacing rates $Rate_{Pacing1}$, $Rate_{Pacing2}$. The region selection unit 410 is further configured to compare the first rate of change with the second rate of change and identify the region representing an inadequate repolarization rate at the one or more of the anatomical locations based on the comparison of the first and second rates of change. During operation, the comparison of the first and second rates of change (e.g., a percentage change) is analyzed to identify abnormally functioning tissues of the heart that are not recovering as fast as other normally functioning tissues. As such, the region selection unit 410 identifies unhealthy regions of the heart whose repolarization rates are not fast enough to adapt to the pacing rate changes. For example, the repolarization rate of the heathy tissues is commensurate with the pacing rate change, but the repolarization rate of the unhealthy tissues cannot adapt to the pacing rate change (i.e., slower in reaction).

Figure 8:
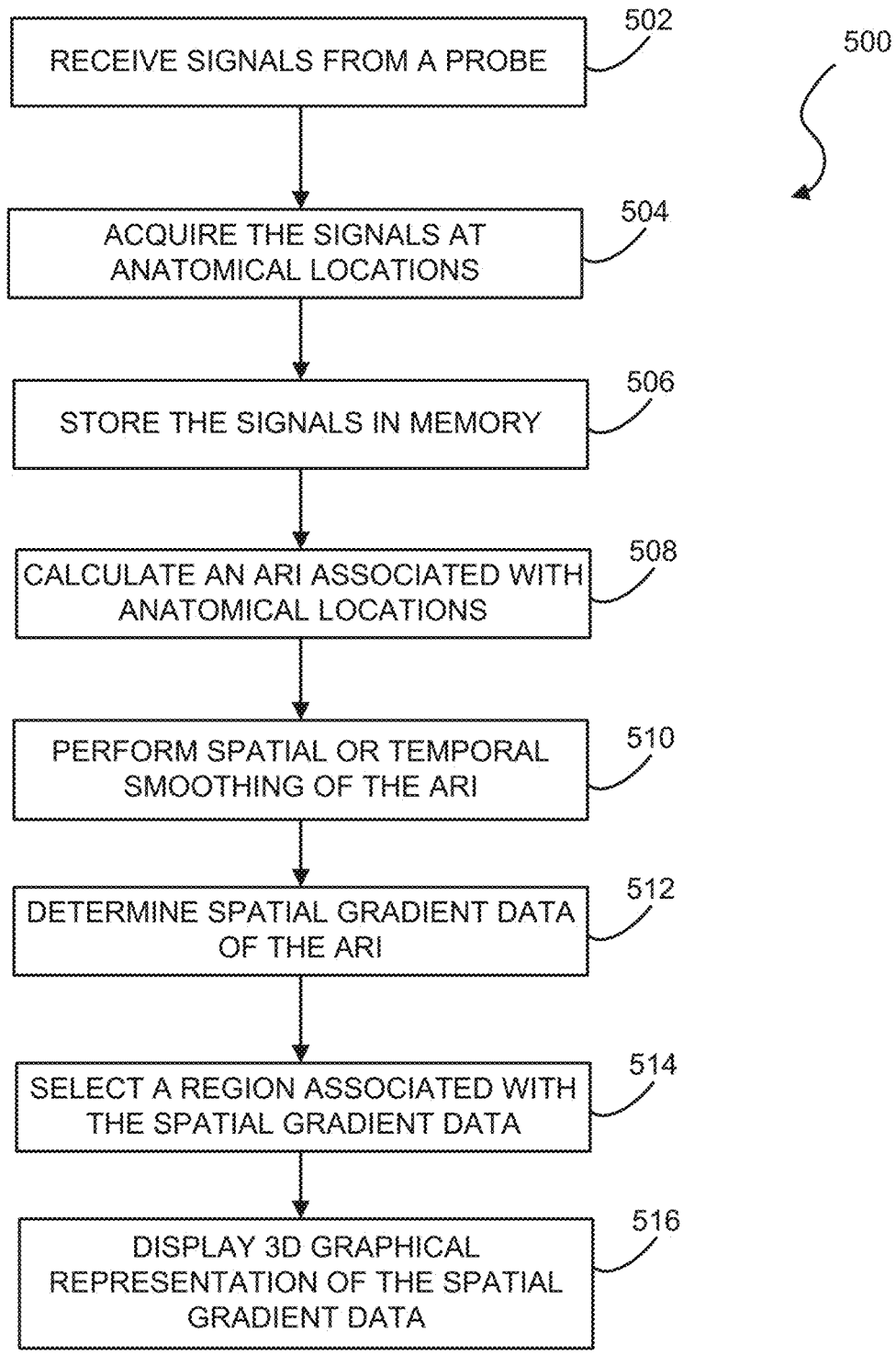
FIG. 8 is a flow diagram depicting an illustrative method of a first exemplary repolarization mapping process of the repolarization mapping unit of FIG. 6, in accordance with embodiments of the disclosed subject matter.

FIG. 8 is a flow diagram depicting an illustrative method 500 of a first exemplary repolarization mapping process of the repolarization mapping unit 134 of FIG. 6 in accordance with embodiments of the disclosed subject matter. As shown in FIG. 8, embodiments of the method 500 include receiving one or more signals from the mapping probe 14 of FIG. 1. In particular embodiments, at a plurality of signal-acquiring times, a plurality of electrogram signals $S_{1-N}$ of a body chamber are acquired using one or more electrodes 24 disposed on the mapping probe 14 at a plurality of anatomical locations within the body chamber (block 504). Each electrogram signal relates to three-dimensional positional data corresponding to the plurality of anatomical locations for each of the plurality of electrodes 24.

In embodiments, the plurality of electrogram signals $S_{1-N}$ of the body chamber corresponding to electrical activities sensed at the one or more electrodes 24 at corresponding anatomical locations are stored in memory 230 at the plurality of signal-acquiring times (block 506). In embodiments, based on each of the plurality of electrogram signals $S_{1-N}$ of the body chamber, an activation recovery interval associated with each of the corresponding anatomical locations is calculated (block 508).

In embodiments, at least one of spatial smoothing and temporal smoothing of the ARI between at least two neighboring anatomical locations is performed for providing a gradual change of the activation recovery interval on the display device 270 (block 510). In embodiments, for each corresponding anatomical location, spatial gradient data of the activation recovery interval is determined based on a distance between at least two neighboring anatomical locations (block 512). In embodiment, a region associated with the spatial gradient data satisfying a predetermined selection standard is selected for display on the display device 270 (block 514). In embodiments, a three-dimensional graphical representation of the spatial gradient data of the activation recovery interval between the at least two neighboring anatomical locations is displayed on the display device 270 (block 516).

In embodiments, blocks 502 to 516 of the repolarization mapping process are carried out continuously and repetitively over a succession of time steps that collectively define a larger time interval. In embodiments, the larger time interval may correspond to at least a portion of a medical procedure.

Figure 9:
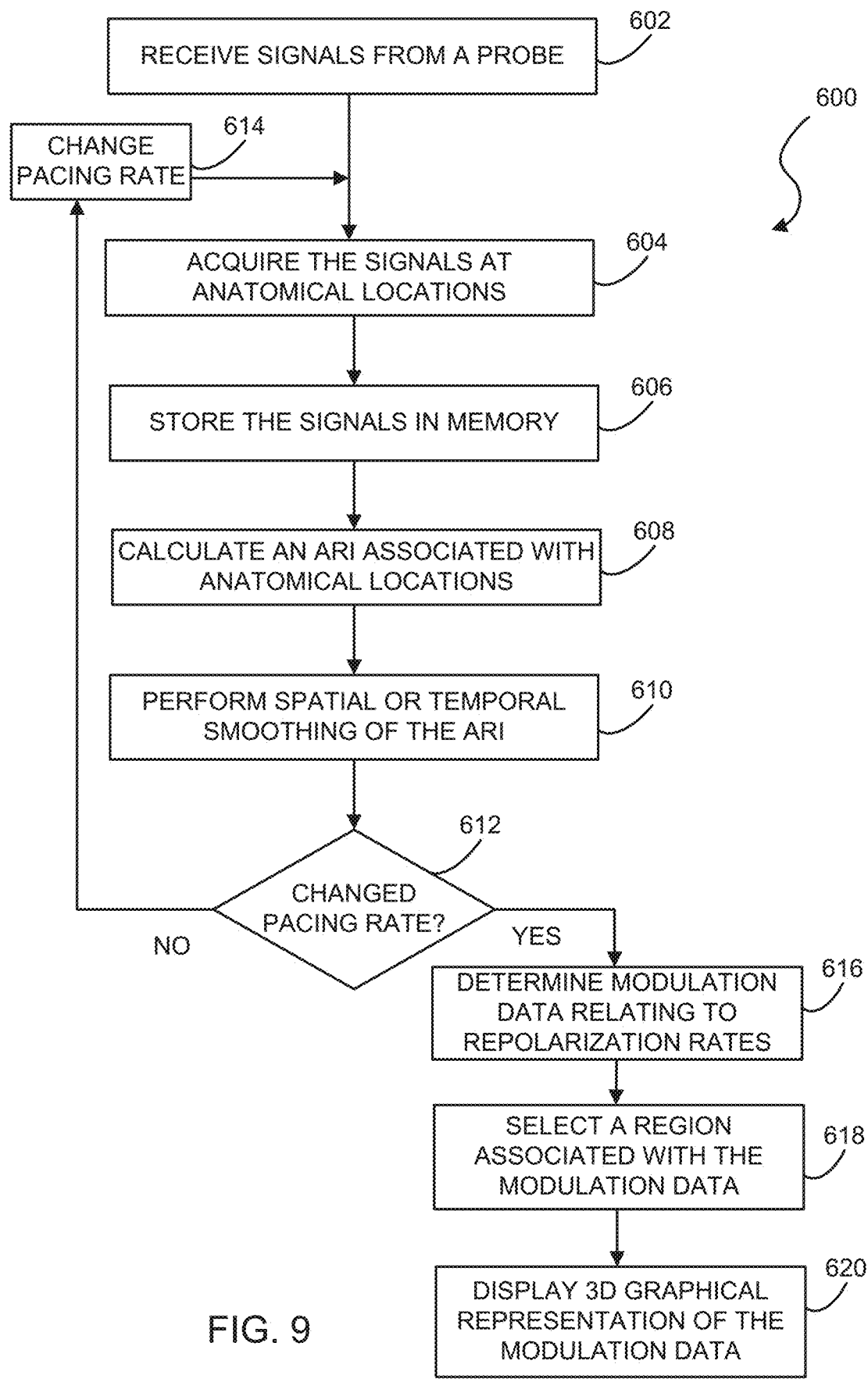
FIG. 9 is a flow diagram depicting an illustrative method of a second exemplary repolarization mapping process of the repolarization mapping unit of FIG. 7.

FIG. 9 is a flow diagram depicting an illustrative method 600 of a second exemplary repolarization mapping process of the repolarization mapping unit 134' of FIG. 7. As shown in FIG. 9, embodiments of the method 600 include receiving one or more signals from the mapping probe 14 In particular embodiments, at a plurality of signal-acquiring times at a first pacing rate $Rate_{Pacing1}$ of a heart, a first plurality of electrogram signals $S_{1-N}$ of a body chamber using one or more electrodes 24 at a plurality of anatomical locations within the body chamber (block 604). Each first electrogram signal relates to three-dimensional positional data corresponding to the plurality of anatomical locations for each of the plurality of electrodes 24.

In embodiments, the first plurality of electrogram signals $S_{1-N}$ of the body chamber corresponding to electrical activities sensed at the one or more electrodes 24 at corresponding anatomical locations are stored in memory 230 at the plurality of signal-acquiring times at the first pacing rate $Rate_{Pacing1}$ (block 606). In embodiments, based on each of the first plurality of electrogram signals $S_{1-N}$ of the body chamber, a first activation recovery interval associated with each of the corresponding anatomical locations at the first pacing rate $Rate_{Pacing1}$ is calculated (block 608).

In embodiments, at least one of spatial smoothing and temporal smoothing of the ARI between at least two neighboring anatomical locations is performed for providing a gradual change of the activation recovery interval on the display device 270 (block 610). At block 612, when the first pacing rate $Rate_{Pacing1}$ has not been changed after a predetermined time period, control proceeds to block 614 to change the first pacing rate $Rate_{Pacing1}$ to the second pacing rate $Rate_{Pacing2}$. In one embodiment, the second pacing rate $Rate_{Pacing2}$ is faster than the first pacing rate $Rate_{Pacing1}$. However other suitable second pacing rates having different speeds are also contemplated to suit different applications.

Control returns to repeat blocks 604-610 for the second pacing rate $Rate_{Pacing2}$. In embodiments, at the plurality of signal-acquiring times at the second pacing rate $Rate_{Pacing2}$ of the heart, a second plurality of electrogram signals $S'_{1-N}$ of the body chamber is acquired using the electrodes 24 at the plurality of anatomical locations within the body chamber (block 604). Similarly, the second plurality of electrogram signals $S'_{1-N}$ of the body chamber corresponding to the electrical activities sensed at the electrodes 24 at the corresponding anatomical locations are stored in memory 230 at the plurality of signal-acquiring times at the second pacing rate Rate$_{Pacing2}$ (block 606). In embodiments, based on each of the second plurality of electrogram signals S'$_{1-N}$ of the body chamber, a second activation recovery interval associated with each of the corresponding anatomical locations at the second pacing rate Rate$_{Pacing2}$ is calculated (block 608). Another spatial or temporal smoothing of the ARI between at least two neighboring anatomical locations may be performed for providing the gradual change of the ARI on the display device 270 (block 610).

At block 612, since the first pacing rate Rate$_{Pacing1}$ has been changed to the second pacing rate Rate$_{Pacing2}$, control proceeds to block 616. In embodiments, for each corresponding anatomical location, modulation data relating to repolarization rates is determined based on the first and second activation recovery intervals with respect to a cycle length difference between the first and second pacing rates Rate$_{Pacing1}$, Rate$_{Pacing2}$ (block 616). In embodiments, a region associated with the modulation data satisfying a predetermined selection standard is selected for display on the display device 270 (block 618). In embodiments, a three-dimensional graphical representation of the modulation data of the first and second activation recovery intervals between the first and second pacing rates Rate$_{Pacing1}$, Rate$_{Pacing2}$ is displayed on the display device 270 (block 620).

In embodiments, blocks 602 to 620 of the repolarization mapping process are carried out continuously and repetitively over a succession of time steps that collectively define a larger time interval. In embodiments, the larger time interval may correspond to at least a portion of a medical procedure.

While the embodiment just described is performed at two pacing rates, e.g., the first and second pacing rates Rate$_{Pacing1}$, Rate$_{Pacing2}$, in other embodiments three or more pacing rates can be used and the methodology applied accordingly.

It is contemplated that any of the disclosed methods may be implemented across multiple beats, excitations or cardiac pacing time intervals. Further, data collected over multiple heart beats and/or excitations may be analyzed using statistical methodologies and applied to the disclosed methods. For example, activation times may be collected over a series of heart beats and/or pulses. A statistical distribution of the collected activation times may be calculated, analyzed and incorporated into disclosed methods.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A method for displaying physiological mapping data, the method comprising:
   acquiring, at a plurality of signal-acquiring times at a first pacing rate of a heart, a first plurality of electrogram signals of a body chamber at a plurality of anatomical locations within the body chamber, each first electrogram signal relating to three-dimensional positional data corresponding to the plurality of anatomical locations;
   storing, in memory, the first plurality of electrogram signals of the body chamber corresponding to electrical activities at corresponding anatomical locations at the plurality of signal-acquiring times at the first pacing rate;
   calculating, based on each of the first plurality of electrogram signals of the body chamber, a first activation recovery interval associated with each of the corresponding anatomical locations at the first pacing rate;
   acquiring, at the plurality of signal-acquiring times at a second pacing rate of the heart that is faster than the first pacing rate, a second plurality of electrogram signals of the body chamber at the plurality of anatomical locations within the body chamber, each second electrogram signal relating to the three-dimensional positional data corresponding to the plurality of anatomical locations;
   storing, in memory, the second plurality of electrogram signals of the body chamber corresponding to the electrical activities at the corresponding anatomical locations at the plurality of signal-acquiring times at the second pacing rate;
   calculating, based on each of the second plurality of electrogram signals of the body chamber, a second activation recovery interval associated with each of the corresponding anatomical locations at the second pacing rate;
   determining, for each corresponding anatomical location, modulation data relating to repolarization rates based on the first and second activation recovery intervals with respect to a cycle length difference between the first and second pacing rates; and
   displaying a three-dimensional graphical representation of the modulation data of the first and second activation recovery intervals between the first and second pacing rates on a display device.

2. The method of claim 1, wherein determining the modulation data relating to the repolarization rates based on the first and second activation recovery intervals comprises calculating, for each corresponding anatomical location, a derivative of the activation recovery interval.

3. The method of claim 2, further comprising calculating the derivative of the activation recovery interval with respect to a change in the cycle length difference between the first and second pacing rates based on the plurality of signal-acquiring times.

4. The method of claim 1, wherein calculating each of the first and second activation recovery intervals comprises determining an activation time and a recovery time for each corresponding anatomical location based on a corresponding plurality of electrogram signals with respect to corresponding signal-acquiring times, and calculating each activation recovery interval based on a difference between the activation time and the recovery time for each corresponding anatomical location.

5. The method of claim 1, wherein calculating each of the first and second activation recovery intervals comprises performing at least one of spatial smoothing and temporal smoothing of the activation recovery interval between at least two neighboring anatomical locations for providing a gradual change of the activation recovery interval on the display device.

6. The method of claim 1, wherein displaying the three-dimensional graphical representation of the modulation data of the first and second activation recovery intervals comprises selectively displaying a region associated with the modulation data satisfying a predetermined selection standard.

7. The method of claim 6, wherein selectively displaying the region associated with the modulation data comprises displaying the region exhibiting at least one predetermined characteristic of the modulation data between the first and second activation recovery intervals at one or more of the anatomical locations.

8. The method of claim 6, wherein selectively displaying the region associated with the modulation data comprises identifying, for display, the region representing a first rate of change that is less than a predetermined threshold in the repolarization rates between the first and second activation recovery intervals; and calculating a second rate of change between the first and second pacing rates, and wherein identifying the region representing the rate of change in the repolarization rates comprises comparing the first rate of change with the second rate of change and identifying the region representing an inadequate repolarization rate at the one or more of the anatomical locations based on the comparison of the first and second rates of change.

9. The method of claim 1, further comprising using three or more pacing rates of the heart for displaying the physiological mapping data.

\* \* \* \* \*